US00PP12912P2

(12) United States Plant Patent
Hill et al.

(10) Patent No.: US PP12,912 P2
(45) Date of Patent: Sep. 3, 2002

(54) CLEMATIS PLANT NAMED 'EVIJOHILL'

(75) Inventors: Josephine Hill, Verwood; Raymond J. Evison, Guernsey, both of (GB)

(73) Assignee: Poulsen Roser International, SARL, Gaillac (FR)

( * ) Notice: Subject to any disclaimer, the term of this patent is extended or adjusted under 35 U.S.C. 154(b) by 51 days.

(21) Appl. No.: 09/219,425

(22) Filed: Dec. 23, 1998

(51) Int. Cl.[7] ..... A01H 5/00

(52) U.S. Cl. ..... Plt./228

(58) Field of Search ..... Plt./228

(56) References Cited

PUBLICATIONS

UPOV–ROM GTITM Computer Database 1999/02, GTI JOUVE Retrieval Software, citations for 'Evijohill', May 1999.*

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

A new compact Clematis cultivar which displays double pink flowers in the form of six long outer tepals with a central rosette of smaller tepals. The variety successfully propagates from softwood cuttings and is suitable for ornamental use in outdoor settings in a variety of climatic conditions. This new and distinct variety has shown to be uniform and stable in the resulting generations from asexual propagation.

1 Drawing Sheet

BACKGROUND OF THE INVENTION

The present invention relates to a new and distinct cultivar of *Clematis hybrida* plant hereinafter referred to by the cultivar name 'Evijohill'. Clematis comprises over 200 species of perennial herbs or woody climbing vines. Many members of this genus and prized as ornamentals. Of particular importance are members which are large-flowered vines planted for permanent cover of fences or trellises. The woody vines can be divided (for the ease of cultivation) into three groups and include (1) the alpina, macropetala and montana groups which flower directly from the previous season's stems in spring, (2) the early, large-flowered cultivars which flower from old wood in the spring and later on new growth, and (3) the later-flowering, large-flowered cultivars and other species which flower on new growth in summer and autumn.

'Evijohill' was discovered by Josephine Hill in a cultivated area. The mutation resulted from a naturally occurring mutation of unknown causation on a Clematis plant growing in a cultivated area. The resulting mutation was evaluated and asexually propagated in a controlled environment. 'Evijohill' was selected as a single plant by Raymond J. Evison in his Clematis development program in Domarie Vineries Les Sauvagees, St. Sampsons, Guernsey, Channel Islands, United Kingdom in 1994 from among plant selections esexually propagated from the originally selected mutant.

The following unique combination of characteristics that are outstanding in 'Evijohill' have been repeatedly observed in asexually propagated progeny and distinguish it from all other varieties of which we are aware:

1. A double flower with 6–8 outer tepals which surround a central cluster of smaller tepals which open more slowly.

2. Superb flower longevity. Inner tepals continue to open after outer tepals have fallen away.

3. No anthers, style or stigma.

4. Long recurrent flowering period from early summer through autumn.

5. Compact growth making the variety suitable for growing in containers.

This combination of qualities is not present in previously available commercial cultivars of this type and distinguishes 'Evijohill' from all other varieties of which we are aware.

Asexual reproduction of 'Evijohill' by cuttings was first done by Raymond J. Evison in Domarie Vineries Les Sauvagees, St. Sampsons, Guernsey, Channel Islands, United Kingdom in 1994. This initial propagation, and subsequent propagations, have demonstrated that the characteristics of 'Evijohill' are true-to-type and are transmitted from one generation to the next.

BRIEF DESCRIPTION OF THE DRAWING

The accompanying photographic drawing shows typical characteristics of the buds, flowers and leaves of 'Evijohill', with different flowers shown in various stages of maturity, depicted in color as nearly true as possible with illustrations of this type. The flower form, flower colors, flower buds, floral parts, flower pedicels and the cultivar's foliage are depicted. Specifically illustrated in Sheet 1 is (1) stem showing branching and the attachment of leaves, nodes, and a bud; (2) flower buds and pedicels; (3) partially open flower bud; (4) the upper flower being completely open, the lower flower being less developed; (5) reverse side of flower; (6) single leaf; and (7) petiolule and leaflets.

The color references used herein employ terminology in accordance with The Royal Horticultural Society (R.H.S.) London, England) Colour Chart, 1995, except where common terms of color are used.

DETAILED BOTANICAL DESCRIPTION

The following is a detailed description of 'Evijohill', as observed in its growth throughout the flowering period in glasshouses at Domarie Vineries Les Sauvagees, St. Sampsons, Guernsey, Channel Islands, United Kingdom and in a nursery in Jackson County, Oregon. Certain phenotypical characteristics of the variety may vary under different environmental, cultural, agronomic, seasonal, and climatic conditions without a change in the genotype of the cultivar.

Parentage: Mutation.
Classification:
*Botanical.*—*Clematis hybrida.*
*Commercial.*—Double flowered compact cultivar.

Flower and Flower Bud

Blooming habit: Recurrent, Summer through Fall
Flower bud:
*Size.*—20 mm–25 mm in length.
*Form.*—Short and ovoid.
*Color.*—Green (143C R.H.S.) at ¼ opening.
*Tepals.*—Outer tepal color is Purple (76B R.H.S.).
*Peduncle.*—Surface: Smooth. Length: 50 mm–100 mm average length. Color: Medium green (143C R.H.S.). Strength: Erect.
*Borne.*—Singly.
Flower bloom:
*Size.*—Medium. 140 mm across outer tepals and 80 mm across inner tepals.
*Number of blooms per plant.*—Typically 15–20 (two year old plant).
*Form.*—Convex. Completely open outer tepals are flat. Inner tepals generally do not open completely.
*Color.*—Upon opening, the upper surface in pink/purple (69B with a central greyed green color of the unopened tepals (195B–195D). Upon opening, the reverse side is Green (143C R.H.S.). After opening, the upper surface is Purple (76C R.H.S.). After opening, the reverse surface is Purple (76D R.H.S.). The base of the tepals is White (155C R.H.S.). The general tonality of the open flower is Red-Purple (68C R.H.S.). The upper surface on the outermost tepals has a center bar of Red-Purple (72C R.H.S.). The reverse surface has a central bar Green (143C R.H.S.).
*Fragrance.*—None.

Lasting quality of flowers on plant and as a cut flower is very long compared to other Clematis cultivars.

Tepals:
*Lastingness of the bloom.*—Inner tepals: Approx. 4 weeks. Outer tepals: Approx. 7–10 days. Inner and Outer cut tepals: 7 days.
*Tepalage.*—Double. Average range: 50+.
*Shape.*—Individual tepal shape is oblanceolate.
*Cross section.*—Flat.
*Undulation of margin.*—Weak.
*Tepal apex.*—Narrowly acute.
*Persistence.*—Outer tepals drop off cleanly, inner tepals persist.
*Arrangement.*—Tepals are arranged regularly.
*Margin.*—Tepals: The inner and outer tepals are entire with occasional weak undulated. The inner tepals have a tendency to twist slightly.
Plant:
*Form.*—Climbing and spreading when trellised, otherwise moderately compact.
*Growth.*—Moderately vigorous. Height: When trellised, one season's growth attains 2.5–3.0 meters.
*Stems.*—Color: Young wood: Greyed-Orange (176B R.H.S.). Older wood: Greyed-Purple (187A R.H.S.) to Brown (200A R.H.S.). Hardiness: Similar to other large flowered Clematis varieties, being USDA hardiness zones of 4–9. Internodes: Shape: Cylindrical in cross section. Length: 120 mm–160 mm. Petioles: Size: Average length: Petioles: 50 mm–90 mm. Petiolule: 5 mm–25 mm. Color: Yellow-Green (146C R.H.S.) with intonations of Grey-Orange (172C R.H.S.). Clasping: Clasps by leaf petiolus.
*Bark.*—Young wood: Smooth. Older wood: Smooth.
Foliage: Deciduous. Trifoliate.
*Size.*—Medium. Length 80 mm.
*Quantity.*—Average.
*Color.*—Old Foliage: Upper surface: Green (137A–139A R.H.S.). Lower surface: Green (137C R.H.S.) New Foliage: Upper surface: Yellow-Green (144A R.H.S.). Lower surface: Yellow-Green (144B R.H.S.).
Plant leaves and leaflets:
*Stipules.*—Absent.
*Petiole.*—Length: 50 mm–90 mm. Underneath: Without prickles.
*Leaf edge.*—Terminal leaflet margin is entire.
*Shape.*—Base of leaflet: Rounded. Apex of leaflet: Acute.
*Texture.*—Medium texture. Upper side: Glabrous. Lower side: Ribbed.
*Surface.*—Matte finish.
Reproductive organs: None.
Disease resistance: Similar to other large flowered Clematis varieties.
We claim:
1. A new and distinct variety of Clematis plant, named 'Evijohill' as herein illustrated and described.

* * * * *

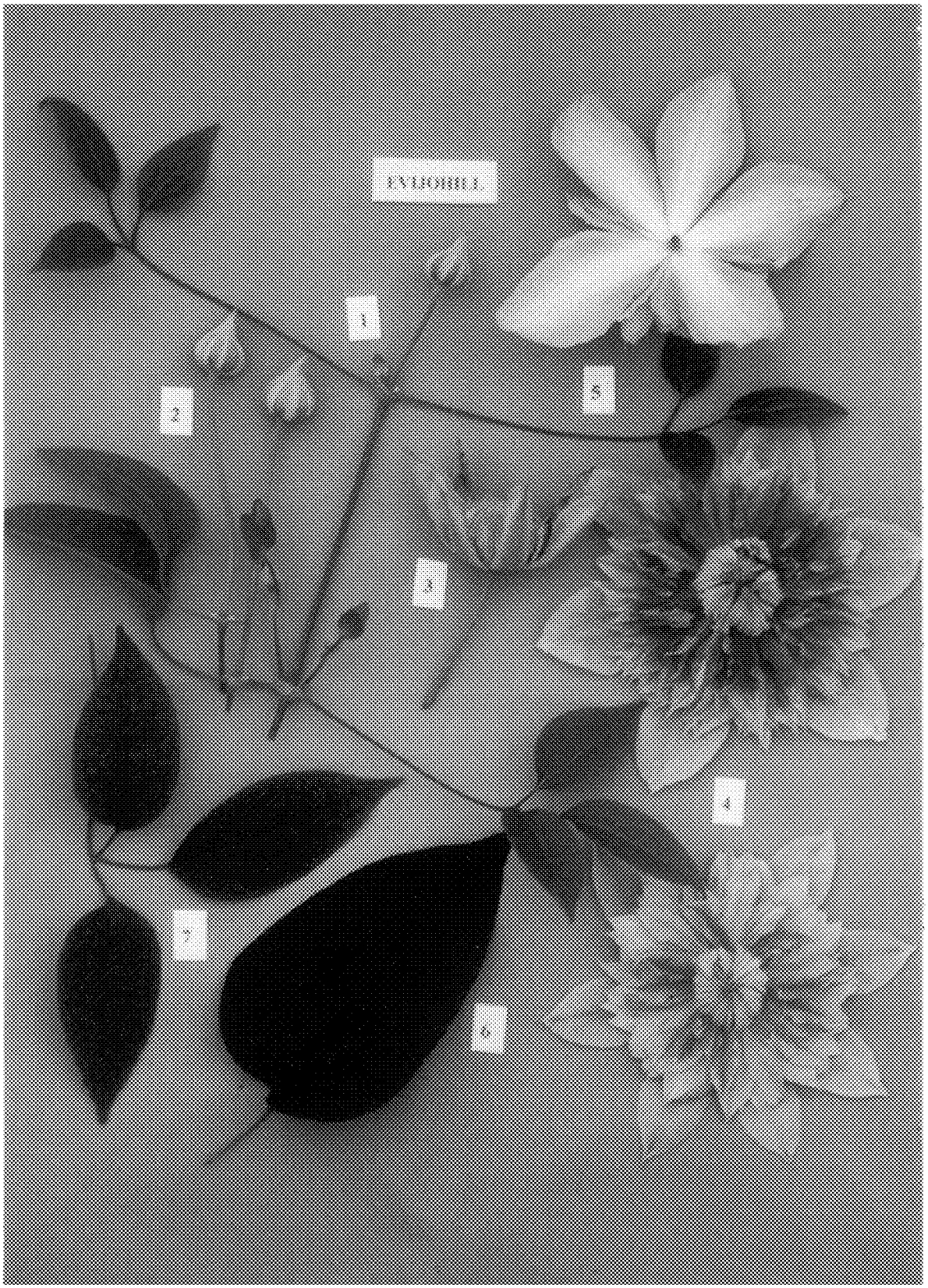
EXHIBIT 1
1
2
3
4
5
6
7